US00PP25363P2

(12) United States Plant Patent
Pineda

(10) Patent No.: US PP25,363 P2
(45) Date of Patent: Mar. 24, 2015

(54) ***THUJA* PLANT NAMED 'MONPIN'**

(50) Latin Name: ***Thuja standishii*×*Thuja plicata***
Varietal Denomination: MonPin

(71) Applicant: Rigoberto Pineda, Salem, OR (US)

(72) Inventor: Rigoberto Pineda, Salem, OR (US)

(73) Assignee: Monrovia Nursery Company, Azusa, CA (US)

( * ) Notice: Subject to any disclaimer, the term of this patent is extended or adjusted under 35 U.S.C. 154(b) by 0 days.

(21) Appl. No.: 13/987,819

(22) Filed: Sep. 7, 2013

(51) Int. Cl.
*A01H 7/00* (2006.01)

(52) U.S. Cl.
USPC ..... Plt./213

(58) Field of Classification Search
USPC ..... Plt./213
See application file for complete search history.

*Primary Examiner* — Anne Grunberg
(74) *Attorney, Agent, or Firm* — C. A. Whealy

(57) ABSTRACT

A new and distinct cultivar of *Thuja* plant named 'MonPin', characterized by its compact and upright plant habit; pyramidal plant form; freely branching habit; dense and bushy form; developing leaves are golden yellow to light yellow green in color becoming darker green with development; and good winter hardiness.

1 Drawing Sheet

Botanical designation: *Thuja standishii*×*Thuja plicata.*
Cultivar denomination: 'MonPin'.

BACKGROUND OF THE INVENTION

The present invention relates to a new and distinct cultivar of *Thuja* plant, botanically known as *Thuja standishii*×*Thuja plicata*, commonly known as Western Arborvitae and hereinafter referred to by the name 'MonPin'.

The new *Thuja* plant is a naturally-occurring whole plant mutation of *Thuja standishii*×*Thuja plicata* 'Green Giant', not patented. The new *Thuja* plant was discovered and selected by the Inventor as a single plant from within a population of plants of 'Green Giant' in May, 2007 in an outdoor nursery in Dayton, Oreg.

Asexual reproduction of the new *Thuja* plant by cuttings in a controlled environment in Dayton, Oreg. since December, 2007, has shown that the unique features of this new *Thuja* plant are stable and reproduced true to type in successive generations.

SUMMARY OF THE INVENTION

Plants of the new *Thuja* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'MonPin'. These characteristics in combination distinguish 'MonPin' as a new and distinct *Thuja* plant:

1. Compact and upright plant habit; pyramidal plant form.
2. Freely branching habit; dense and bushy form.
3. Developing leaves are golden yellow to light yellow green in color becoming darker green with development.
4. Good winter hardiness.

Plants of the new *Thuja* can be compared to plants of the parent, 'Green Giant'. Plants of the new *Thuja* differ primarily from plants of 'Green Giant' in the following characteristics:

1. Plants of the new *Thuja* are more compact than plants of 'Green Giant'.
2. Plants of the new *Thuja* are denser than and not as open as plants of 'Green Giant'.
3. Plants of the new *Thuja* and 'Green Giant' differ in leaf color as developing leaves of plants of 'Green Giant' are bright green in color.

Plants of the new *Thuja* can be compared to plants of *Thuja occidentalis*, 'Brandon', not patented. In side-by-side comparisons, plants of the new *Thuja* differed primarily from plants of 'Brandon' in the following characteristics:

1. Plants of the new *Thuja* were more compact than plants of 'Brandon'.
2. Plants of the new *Thuja* grew slower than plants of 'Brandon'.
3. Plants of the new *Thuja* and 'Brandon' differed in leaf color as developing leaves of plants of 'Brandon' are bright green in color.

BRIEF DESCRIPTION OF THE PHOTOGRAPHS

The accompanying colored photographs illustrate the overall appearance of the new *Thuja* plant showing the colors as true as it is reasonably possible to obtain in colored reproductions of this type. Colors in the photograph may differ slightly from the color values cited in the detailed botanical description which accurately describe the colors of the new *Thuja* plant.

The photograph at the bottom of the sheet comprises a side perspective view of a typical plant of 'MonPin'.

The photograph at the top of the sheet comprises a close-up view of a typical plant of 'MonPin'.

DETAILED BOTANICAL DESCRIPTION

The aforementioned photographs and following observations, measurements and values describe plants grown in five-gallon containers in an outdoor nursery in Dayton, Oreg. and under cultural practices typical of commercial *Thuja* plant production. During the production of the plants, day temperatures ranged from 4° C. to 32° and night temperatures ranged from −2° C. to 15° C. Plants were 44 months old when the photographs and description were taken. In the following detailed description, color references are made to The Royal Horticultural Society Colour Chart, 2007 Edition, except where general terms of ordinary dictionary significance are used.

Botanical classification: *Thuja standishii*×*Thuja plicata* 'MonPin'.

Parentage: Naturally-occurring whole plant mutation of *Thuja standishii*×*Thuja plicata* 'Green Giant', not patented.

Propagation:

*Type*.—By cuttings.

*Time to produce rooted young plants*.—About two to three months at soil temperatures of at 16° C. to 24° C.

*Root description*.—Medium in thickness, fibrous; white in color.

*Rooting habit*.—Moderately freely branching; medium density.

Plant description:

*Plant and growth habit*.—Perennial evergreen shrub; compact plant habit and upright pyramidal plant form; moderately vigorous growth habit; medium to slow growth rate.

*Plant height*.—About 74 cm.

*Plant diameter, base*.—About 48 cm.

*Plant diameter, apex*.—About 4 cm.

*Branching habit*.—Freely branching habit with about 26 lateral branches developing per plant; dense and bushy habit; plants can be sheared to maintain overall plant shape.

*Lateral branch description*.—Length: About 27 cm. Diameter: About 5 mm to 8 mm; main trunk, about 3.2 cm. Internode length: About 2.5 cm to 5.4 cm. Aspect: Main branch, upright; lateral branches curving upward. Strength: Strong. Texture, developing branches: Slightly scaly. Texture, main trunk: Woody. Color: Developing branches: Close to N199C. Developed branches: Close to N199A. Main trunk: Close to 197A to 197B.

*Leaf description*.—Appearance and arrangement: Flattened and closely appressed, scale-like; opposite, simple; sessile. Length: About 6 mm. Width: About 2 mm to 2.5 mm. Shape: Lanceolate. Apex: Acute to apiculate. Base: Truncate. Margin: Entire. Venation pattern: Parallel. Fragrance: When crushed, aromatic and cedar-like. Texture: Smooth, glabrous; glandular. Color: Developing leaves, upper and lower surfaces: Close to 15C becoming closer to N144A with development; during the winter, developing leaves become darker yellow in color with orange red-colored apices. Fully expanded leaves, upper surface: Close to 137B; venation, close to 137B. Fully expanded leaves, lower surface: Close to 137A; venation, close to 137A.

Cone description: Cone development has not been observed on plants of the new *Thuja*.

Temperature tolerance: Plants of the new *Thuja* have been observed have good winter hardiness and to be tolerant to USDA Hardiness Zones 4 to 8 and AHS Heat Zones 1 to 8.

Pathogen & pest resistance: Plants of the new *Thuja* have not been observed to be resistant to pests and pathogens common to *Thuja* plants.

It is claimed:

1. A new and distinct *Thuja* plant named 'MonPin' as illustrated and described.

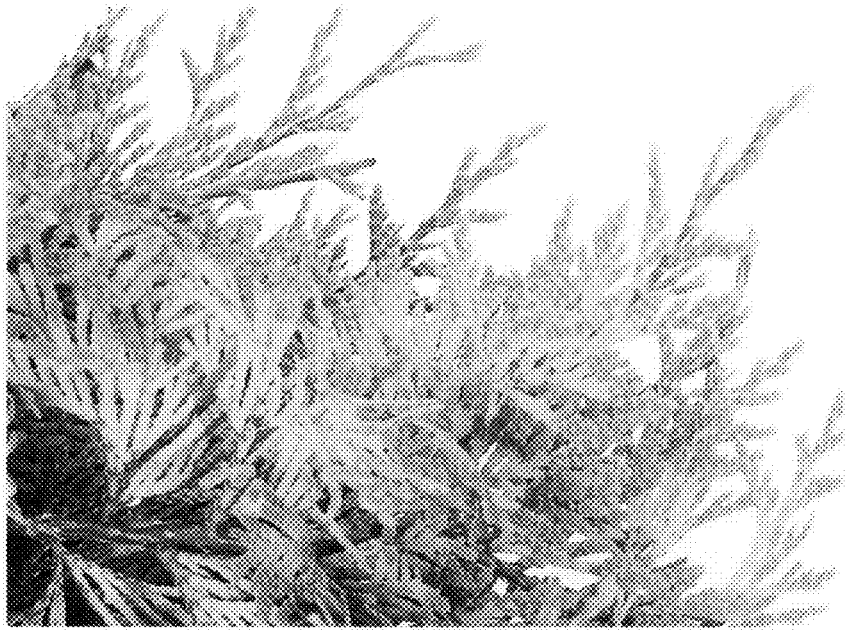
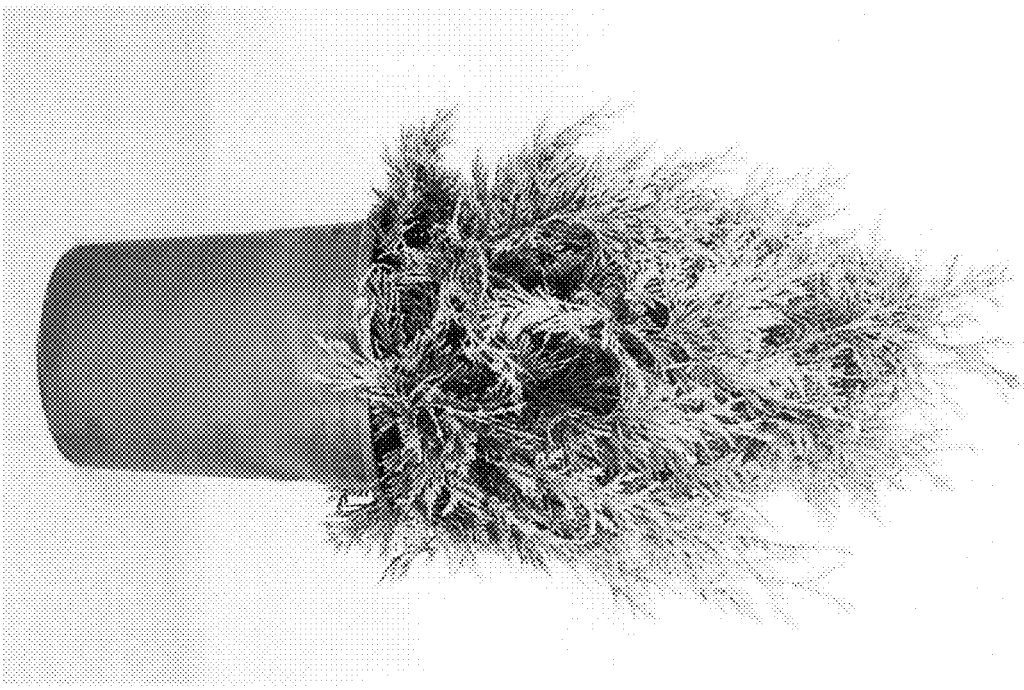

* * * * *